United States Patent [19]

Niazi et al.

[11] Patent Number: 4,639,368

[45] Date of Patent: Jan. 27, 1987

[54] CHEWING GUM CONTAINING A MEDICAMENT AND TASTE MASKERS

[75] Inventors: Sarfaraz Niazi, Oakbrook, Ill.; Alvin Shemesh, Hopkins, Minn.

[73] Assignee: Farmacon Research Corporation, Minneapolis, Minn.

[21] Appl. No.: 741,871

[22] Filed: Jun. 6, 1985

Related U.S. Application Data

[63] Continuation-in-part of Ser. No. 643,584, Aug. 23, 1984.

[51] Int. Cl.$^4$ .............................................. A61K 9/68
[52] U.S. Cl. .......................................... 424/48; 424/44; 426/3
[58] Field of Search ..................................... 424/44, 48

[56] References Cited

U.S. PATENT DOCUMENTS

| | | | |
|---|---|---|---|
| 1,262,888 | 4/1918 | Westlake | 424/44 |
| 1,297,494 | 3/1919 | Rhein | 424/44 |
| 1,630,763 | 5/1927 | Raymer | 424/48 |
| 2,092,742 | 9/1937 | Pauley | 424/44 |
| 2,211,485 | 8/1940 | Zimmerman | 424/44 |
| 2,293,359 | 8/1942 | Quisling | 424/48 |
| 2,627,493 | 2/1949 | Merckel et al. | 424/48 |
| 3,024,165 | 3/1962 | Murphy | 424/44 |
| 3,495,001 | 2/1970 | Leonards | 424/44 |
| 3,590,120 | 6/1971 | Muhler | 424/48 |
| 3,629,468 | 12/1971 | Andersen | 424/44 |
| 3,772,431 | 11/1973 | Mlkvy | 424/44 |
| 3,903,255 | 9/1975 | Gusman et al. | 424/44 |
| 3,962,417 | 6/1976 | Howell | 424/44 |
| 4,112,066 | 9/1978 | Hussein | 424/48 |
| 4,151,270 | 4/1979 | Ream et al. | 424/48 |
| 4,154,814 | 5/1979 | Hand et al. | 424/48 |
| 4,267,164 | 5/1981 | Yeh et al. | 424/44 |
| 4,303,648 | 12/1981 | Witzel et al. | 424/48 |
| 4,400,372 | 8/1983 | Muhler et al. | 424/48 |
| 4,409,202 | 10/1983 | Witzel et al. | 424/48 |
| 4,487,757 | 12/1984 | Kiozpeoplou | 424/44 |
| 4,581,232 | 4/1986 | Peters et al. | 424/155 |

*Primary Examiner*—Shep K. Rose
*Attorney, Agent, or Firm*—Leydig, Voit & Mayer

[57] ABSTRACT

A chewing gum composition adapted to supply a medicament to the oral cavity for local application thereto or for buccal absorption of said medicament which comprises a chewing gum base, an orally administrable medicament, a taste masking generator of carbon dioxide and optionally a taste bud desensitizing composition.

11 Claims, No Drawings

CHEWING GUM CONTAINING A MEDICAMENT AND TASTE MASKERS

RELATED APPLICATION

This is a continuation-in-part of copending U.S. application Ser. No. 643,584, filed on Aug. 23, 1984.

BACKGROUND OF THE INVENTION

1. Field of the Invention

The present invention relates to therapeutic gums; and, more particularly to chewing gum compositions which contain an orally administrable medicament capable of being absorbed, at least in a major proportion, through the buccal cavity, and a taste-masking generator.

2. Description of the Prior Art

Therapeutic compositions have previously been admixed with other ingredients and formed into chewing gum or tablets for oral administration. For example, U.S. Pat. No. 2,536,168 to Goggin discloses a chewing gum product consisting of a gum base enveloped by three layers of materials, the second of which is a layer of amphetamine salt. The layers also contain sucrose and other flavorings to mask the unpleasant taste of the amphetamine salts.

U.S. Pat. No. 3,629,394 to Gaunt et al. discloses chewable tablets consisting of milled rice endosperms into which a water or alcohol soluble drug has previously been absorbed. The endosperms are then admixed with a softener and chewable granulations to form the chewable tablet. The drug is not released in the oral cavity, on the contrary, it is released upon ingestion.

U.S. Pat. No. 3,911,099 to DeFoney et al. discloses a non-chewable tablet which includes an odor masking, analgesic or nitroglycerin-containing composition which is encapsulated with other ingredients. The tablets are then coated with an adhesive and attached to the oral muscosa whereupon the drug is released over a long period of time. It is expressly taught that the tablets may not be chewed, as inadvertent chewing destroys them.

U.S. Pat. No. 4,238,475 to Witzel et al. discloses a chewing gum composition capable of releasing water insoluble therapeutic materials. Although a sweetener is used as a taste-masker, the unpleasant taste of some medicaments may still be overpowering.

Despite the various attempts in the art to incorporate a medicament in a chewing gum base none have been satisfactory, in part, because of the unpleasant taste associated with the release of the medicament from such gums, and, further because the drug or medicament carried by the gum, although administered orally, is typically active only by ingestion of the drug after release caused by chewing the gum product.

Accordingly, it is a principal object of the present invention to provide a pleasant tasting chewing gum product which contains a medicament.

It is a further principal object to provide a medicament containing chewing gum which is capable of readily releasing the medicament so that the medicament can be easily administered orally.

It is a related object of the present invention to provide a chewing gum capable of gradually releasing small portions of the medicament for gradual oral administration of the medicament without the need for ingestion thereof.

It is a further object to provide a medicament-containing chewing gum useful in topical or buccal applications.

Other objects will become apparent to those skilled in the art from reading the specification, examples and claims.

SUMMARY OF THE INVENTION

The present invention provides a chewing gum composition adapted to supply a medicament to the oral cavity for local application thereto or buccal absorption. A gum base provides the carrier for the medicament. The chewing gum composition also contains a carbon dioxide-generating compound and optionally a taste bud desensitizing composition to mask the taste of the medicament.

DETAILED DESCRIPTION OF THE INVENTION

The chewing gum composition of the present invention generally comprises a chewing gum base, an orally administrable medicament, a carbon dioxide-generating compound, that is, a compound or composition capable of generating or releasing carbon dioxide as the gum is chewed, and referred to herein as the carbon dioxide-generator, flavoring and/or sweetening agents, and optionally a taste bud desensitizing composition.

The chewing gum is the carrier for the medicament. The particular gum base selected as the carrier is not critical. Any gum base may be satisfactorily employed so long as it is compatible with the medicament of choice, the selected medicament can be incorporated into the gum, yet can be released upon chewing, and the gum base does not adversely affect the medicament or its operation.

The amount of the gum base is likewise not critical. For example, the gum base may be present in an amount ranging from about 15 weight percent to about 40 weight percent of the total composition. Many formulations are possible depending upon the type of gum product desired and the selected medicament. Suitable raw materials for the gum base are well known in the art and include chicle, latex, RBH resin, crown gum, Malsa compound PU-C, picolyte resin, candelilla wax, chiquibil gum and other known gum bases.

Conventional chewing gum bases that may be obtained from commercial suppliers are also suitable for use in the present invention. For example, stick gum or bubble gum may be utilized. Stick gum is generally preferred for the reason that it is less likely to be mistakenly ingested by children. Suitable conventional stick gum bases include "Paloja," "Firm Paloja," "Berguna" and "Dreyco," available from the C. A. Dreyfus Corporation, and "Synthetic Base No. 2939" and Natural Base No. SC319, available from the American Chicle Company.

In addition to the gum base, the composition of the present invention may also contain other nonactive materials, such as sweeteners, flavoring components and fillers.

Any conventional sweetener or flavoring component may be used. Combinations of sweeteners, flavoring components, or sweeteners and flavoring components may likewise be used. Natural or artificial flavors such as spearmint, peppermint, cinnamon, wintergreen or the like can be satisfactorily included in the gum product. Sweeteners useful in the present invention include sorbitol, synthetic sweetening agents such as saccharin, aspartame or other sugar alcohols, and natural sweeteners such as corn syrup or sugar. In the preferred embodiment, the majority of the sweetener is provided by synthetic or non-nutritive sweeteners to avoid the excessive calories inherent in natural sweeteners. In general, the sweetener and/or flavoring component is present in an amount sufficient to provide a generally pleasant taste to the gum product. Thus, for example, the amount of sweetener or flavoring agent may range from about 40 weight percent to about 70 weight percent of the total weight of the final gum product.

Inert filler materials may also be added to provide advantageous consistency effects to the chewing gum compositions of the present invention. Any filler known in the art may be used, such as, for example, mannitol, glycerin, lecithin, or the like.

In accordance with the present invention, the medicaments or drugs suitable for use in the composition of the present invention must be capable of being absorbed into the bloodstream from or through the buccal cavity without undergoing decomposition or alteration. In addition, the medicament or drug must not significantly irritate buccal mucosa. Medicaments which undergo first pass metabolism following oral administration are preferred. As used herein, the term medicament includes any drug, pharmaceutical or medicine suitable for use in the treatment of human pain, ailments, disease or conditions, such as obesity. The medicament or drug is gradually released from the gum composition in relatively small amounts as a result of the chewing action. The amount released is sufficiently small that the major portion of the medicament released is absorbed through the buccal cavity. Continued chewing of the gum until it is spent, that is, until most or all of the medicament has been released, will provide at least the requisite dosage of the medicament to treat the ailment or symptom for which the gum composition was prescribed. Only a small portion of the medicament, or none at all, is ingested, the amount ingested typically being so slight as to not appreciably aid in the treatment of the ailment or symptom. Stated another way, the medicament is gradually released by the chewing action such that a small amount of the medicament is absorbed into the bloodstream through the buccal cavity and chewing is continued until most or all of the medicament has been released. The total amount of medicament absorbed into the bloodstream through the buccal cavity is thus effective for treating the ailment or symptom for which the gum was designed, including, for example, such varied symptoms as sinusitis, indigestion, diarrhea, obesity, and the like.

In comparison with medicament-containing gums or tablets in which ingestion is the mechanism relied upon for absorbing the medicament into the bloodstream, the gum composition of the present invention is faster acting. Also because of the generally more efficient mechanism of absorbing the medicament into the bloodstream resulting from the use of medicaments which are capable of being absorbed buccally, a lesser amount of the medicament is needed than would otherwise be required if ingestion is relied upon. As a result, undesirable side effects can be avoided.

It will thus be appreciated that the medicament-containing gum of the present invention will find utility in a wide variety of applications. For example, it can be suitably employed in many clinical applications, especially, for example, where the patient cannot swallow, where rapid response is needed or desired, and where the drug is metabolized or decomposed in the gastrointestinal tract and larger doses than desired would otherwise be required if the drug was administered by ingestion. Alternatively, the gum may be used in the treatment of long term illnesses, or where a delayed response is desired.

The chewing gum product of the present invention can likewise be used for local application to the oral cavity, such as, for example, for the treatment of canker sores, carcinoma of the mouth and the like.

Many types of medicaments can be utilized in the chewing gum product of the present invention, provided, for the reasons set forth above, that the compound is capable of being absorbed, at least in major part through the buccal cavity. Exemplary of the many medicaments suitable for use in the chewing gum composition of the present invention are analgesics, such as ibuprofen and acetominophen; laxatives, such as phenolphthalein dioctysodiumsulfosuccinate; anorexics, such as amphetamines and phenylpropanolamine; antacids, such as calcium carbonate; antiasthmatics, such as theophylline; antidiarrhetics, such as diphenoxylate hydrochloride; antiflatulents such as simethecon; antimigraine agents such as ergotamine tartarate; antipsychotics, such as haloperiodol; antispasmodics or sedatives, such as phenobarbitol (with or without atropine); antihyperactive, such as methyldopa and methylphenidate; tranquilizers, such as benzodiazepines, hydroxyzine meprobamates and phenothiazines; antihhistaminic agents, such as chlorpheniramine maleate, pyridamine maleate, doxylamine succinate, bromopheniramine maleate, phenyltoloxamine citrate, chlorcyclizine hydrochloride and pheniramine maleate; decongestants such as phenylpropanolamine HCl, phenylephrine HCl, phenylpropanolamine bitathate, and the sulfate or hydrochloride of pseudoephidrine; beta blockers, such as propanolol; anti-alcoholism agents, such as disulfiram; cough suppressants, such as benzocaine and dextromethorpane; flouride supplements, such as sodium fluoride; local antibiotics, such as tetracycline and cleocin; corticosteroid suppliers, such as prednisone/prednisolone; anti-goiter agents, such as colchicine and allopurinol; anti-epileptics, such as phenytoin sodium; anti-dehydration agents, such as electrolyte supplements; antiseptics, such as cetyl pyridinium chloride; anticavity agents, such as urea; and the like.

Other suitable medicaments include, nitroglycerin, nystatin, estra-1,3,5(10)-triene-3,17-B-diol,1-(p-chloro-d-phenylbenzyl)-4-(m-methylbenzyl)hydrochloride, progesterone, testosterone, ascorbic acid, vitamin B12, and trace mineral supplements, clotrimazole and ketoconazole.

The amount of medicament utilized will vary depending upon the particular drug selected and the symptom or ailment being treated. The dosage included in the gum composition must be sufficient to provide therapeutic blood levels of the medicament. In general, the amount may vary widely, typically, from about 0.5 milligrams of medicament per stick of chewing gum composition to about 500 milligrams of drug per stick of chewing gum composition.

Many of the medicaments useful in the present invention have an unpleasant taste. Thus, it is preferred to mask the taste. Natural and/or artifical sweeteners may be used, but are not entirely satisfactory because the taste of the medicament is often so strong that it overpowers the sweetener. However, the taste of the medicament may be effectively masked by the use of compounds or mixtures capable of generating carbon dioxide.

The carbon dioxide generator of the present invention produces a local, topical anaesthetic effect that serves to mask any undesirable off-taste that may result from the release of the medicament into the mouth. The carbon dioxide can be provided via an effervescent reaction between, for example, a water soluble bicarbonate salt, such as sodium bicarbonate, and an organic acid suitable for human comsumption, such as tartaric acid when the gum composition is chewed. Each of these materials is preferably a solid, and is incorporated into the chewing gum base as fine granular particles, preferably not greater than ten microns particle size.

Carbonated candy can also be used as a carbon dioxide generator alone or in combination with another effervescent composition. This candy may also serve as a substitute for sweeteners or flavoring agents that might otherwise be added to the chewing gum composition of the present invention.

If the medicament has a particularly strong, unpleasant taste and an additional taste masking effect is desired, an oral topical anaesthetic may be added to the chewing gum composition of the present invention. Any oral anesthetic may be used, so long as it is compatible with and does not interfere with the medicament. Suitable oral anaesthetics include benzocaine and spilanthol. The amount of oral anaesthetic utilized can be up to 5 mg/individual portion, such as a stick or the like, of chewing gum base with an amount between about 1 mg/portion and about 3 mg/portion being preferred. Generally, use of the oral anaesthetic in an amount less than 1 mg/portion will have little or no taste-masking effect.

The following Examples are intended to further illustrate the invention which is described herein and are not intended to limit the scope thereof.

As used in the examples, the following designations, symbols, terms and abbreviations have the following meanings.

NutraSweet ® is a registered trademark of G. D. Searle & Co. referring to a brand of aspartame, a non-nutritive sweetener.

The chewing gum compositions were prepared in accordance with the following procedure with the exception that an oral anaesthetic was not used in Examples 2 and 4. The amount of each ingredient used is given in the specific examples.

The gum base was admixed with corn syrup in a vessel and slowly warmed with stirring to approximately 175° F. Filler and sweetener were then blended with vigorous stirring. Flavoring was then added with further stirring for approximately 5 to 10 minutes, after which an oral anaesthetic and the selected medicament were added with final vigorous stirring for no more than about 5 minutes. The mixture was then permitted to cool for 2 minutes and then shaped into the desired stick form.

EXAMPLE 1

This Example illustrates a chewing gum composition of the present invention which contains two medicaments, an antihistaminic agent and a decongestant. The amount of each ingredient used per stick of chewing gum is set forth in Table I.

TABLE I

| Constituent | Weight |
| --- | --- |
| gum base | 5 gms. |
| benzocaine | 2.5 mg. |
| phenylpropanolamine HCl | 20 mg. |
| chlorpheniramine maleate | 2.5 mg. |
| corn syrup | 30 gms. |
| mannitol | q.s. |
| spearmint flavoring | q.s. |
| sodium bicarbonate | 50 mg. |
| tartaric acid | 50 mg. |
| NutraSweet ® | q.s. |

The chewing gum formed from the above composition had a pleasant consistency and could be chewed for approximately 10-15 minutes without any unpleasant sensation. In addition, the use of the gum produced the desired antihistaminic and decongestant effect.

EXAMPLE 2

This Example illustrates a chewing gum composition which contains two medicaments, an antihistaminic agent and a decongestant. The amount of each ingredient used per stick of chewing gum is set forth in Table II.

TABLE II

| Constituent | Weight |
| --- | --- |
| gum base | 5 gms. |
| chlorpheniramine maleate | 3 mg. |
| phenylpropanolamine HCl | 10 mg. |
| phenylephrine HCl | 30 gms. |
| corn syrup | 30 gms. |
| sorbitol | q.s. |
| peppermint oil | q.s. |
| sodium bicarbonate | 250 mg. |
| tartaric acid | 250 mg. |
| sodium saccharine | 0.5 gms. |

The use of the gum composition produced the desired antihistaminic and decongestant effect.

EXAMPLE 3

This Example illustrates the chewing gum composition of the present invention with an anorexic (phenylpropanolamine) as the medicament. The amount of each ingredient used per stick of chewing gum is set out in Table III.

TABLE III

| Constituent | Weight |
| --- | --- |
| gum base | 5 gms. |
| benzocaine | 2.5 mg. |
| phenylpropanolamine | 50 mg. |
| corn syrup | 30 gms. |
| mannitol | q.s. |
| spearmint flavoring | q.s. |
| sodium bicarbonate | 250 mg. |
| tartaric acid | 250 mg. |
| NutraSweet ® | q.s. |

The chewing gum formed from the above composition had a pleasant consistency and could be chewed for 10-15 minutes without any unpleasant sensation. In addition, the use of the gum produced the desired anorexic effect.

EXAMPLE 4

This Example illustrates the chewing gum composition of the present invention with an anorexic as the medicament. The amount of each ingredient used per stick of chewing gum is set out in Table IV.

TABLE IV

| Constituent | Weight |
| --- | --- |
| gum base | 5 gms. |
| phenylpropanolamine HCl | 50 mg. |
| corn syrup | 30 gms. |
| sorbitol | q.s. |
| peppermint oil | q.s. |
| sodium bicarbonate | 250 mg. |
| tartaric acid | 250 mg. |
| sodium saccharine | 0.5 gms. |

The use of the gum composition produced the desired anorexic effect.

We claim:

1. A chewing gum composition adapted to supply a medicament to the oral cavity comprising, a chewing gum base, an orally administrable medicament capable of being absorbed through the buccal cavity, said medicament consisting essentially of phenylpropanol amine, and a carbon dioxide generator.

2. The chewing gum composition of claim 1 wherein the carbon dioxide generator consists essentially of a mixture of a water soluble bicarbonate salt and an organic acid suitable for human consumption.

3. The chewing gum composition of claim 2 wherein said bicarbonate salt is sodium bicarbonate and said organic acid is tartaric acid.

4. A chewing gum composition adapted to supply a medicament to the oral cavity comprising, a chewing gum base, a flavoring agent, an orally administrable medicament consisting essentially of phenylpropanol amine, and a taste-masking material selected from the group consisting of a carbon dioxide generator and a taste bud desensitizing composition.

5. The chewing gum composition of claim 4 wherein the carbon dioxide generator consists essentially of a mixture of a water soluble bicarbonate salt and an organic acid suitable for human consumption.

6. The chewing gum composition of claim 5 wherein said bicarbonate salt is sodium bicarbonate and said organic acid is tartaric acid.

7. The chewing gum composition of claim 4 wherein said flavoring agent is a non-nutritive sweetener.

8. The chewing gum composition of claim 4 wherein said flavoring agent is a natural sweetener.

9. The chewing gum composition of claim 5 wherein said taste bud desensitizing composition is benzocaine.

10. The chewing gum composition of claim 5 wherein said taste bud desensitizing composition is spilanthol.

11. A chewing gum composition adapted to supply a medicament to the oral cavity comprising a chewing gum base, an orally administrable medicament capable of being absorbed through the buccal cavity, said medicament consisting of phenylpropanol amine, a taste masking generator of carbon dioxide consisting essentially of a mixture of sodium bicarbonate and tartaric acid, and a taste bud desensitizing composition selected from the group consisting of benzocaine and spilanthol.

* * * * *